United States Patent [19]
Audousset et al.

[11] Patent Number: 6,022,382
[45] Date of Patent: *Feb. 8, 2000

[54] PROCESSES AND KITS FOR DYEING KERATINOUS FIBERS WITH A PARA-PHENYLENEDIAMINE CONTAINING A PRIMARY, SECONDARY OR TERTIARY AMINE FUNCTION, A META-PHENYLENEDIAMINE, AND A PARA-AMINOPHENOL OR A META-AMINOPHENOL

[75] Inventors: Marie-Pascale Audousset, Asnieres; Jean Cotteret, Verneuil S/Seine, both of France

[73] Assignee: L'Oreal, Paris, France

[*] Notice: This patent is subject to a terminal disclaimer.

[21] Appl. No.: 09/232,850

[22] Filed: Jan. 19, 1999

Related U.S. Application Data

[63] Continuation of application No. 08/712,183, Sep. 11, 1996, Pat. No. 5,863,300, which is a continuation of application No. 08/361,661, Dec. 22, 1994, abandoned.

[30] Foreign Application Priority Data

Jan. 24, 1994 [FR] France .................. 9400701

[51] Int. Cl.$^7$ .................................. A61K 7/13
[52] U.S. Cl. ..................... 8/411; 8/406; 8/408; 8/412
[58] Field of Search .................... 8/405, 406, 410, 8/411, 412, 416, 421, 408

[56] References Cited

U.S. PATENT DOCUMENTS

| | | | |
|---|---|---|---|
| 3,884,627 | 5/1975 | Brody et al. | 8/410 |
| 4,125,367 | 11/1978 | Bugaut et al. | 8/411 |
| 4,277,244 | 7/1981 | Bugaut et al. | 8/411 |
| 4,314,809 | 2/1982 | Rose et al. | 8/421 |
| 4,323,360 | 4/1982 | Bugaut et al. | 8/411 |
| 4,324,553 | 4/1982 | Bugaut et al. | 8/411 |
| 4,330,292 | 5/1982 | Bugaut et al. | 8/411 |
| 4,333,730 | 6/1982 | Bugaut et al. | 8/421 |
| 4,357,141 | 11/1982 | Grollier et al. | 8/406 |
| 4,692,166 | 9/1987 | Junino et al. | 8/410 |
| 4,736,067 | 4/1988 | Bugaut et al. | 8/407 |
| 4,854,935 | 8/1989 | Clausen et al. | 8/411 |
| 4,863,480 | 9/1989 | Bugaut et al. | 8/421 |
| 4,883,656 | 11/1989 | Konrad et al. | 8/412 |
| 4,904,275 | 2/1990 | Grollier et al. | 8/411 |
| 5,053,052 | 10/1991 | Junino et al. | 8/412 |
| 5,202,487 | 4/1993 | Junino et al. | 8/411 |

FOREIGN PATENT DOCUMENTS

| | | |
|---|---|---|
| 359618 | 3/1990 | European Pat. Off. . |
| 2362112 | 3/1978 | France . |
| 2519251 | 7/1983 | France . |
| 3016109 | 11/1980 | Germany . |
| 3022792 | 1/1981 | Germany . |
| 3100477 | 12/1981 | Germany . |
| 3125705 | 3/1982 | Germany . |
| 3609504 | 10/1986 | Germany . |
| 3914394 | 10/1990 | Germany . |
| 2018808 | 10/1979 | United Kingdom . |
| 2025958 | 1/1980 | United Kingdom . |
| 2054663 | 2/1981 | United Kingdom . |
| 2078747 | 1/1982 | United Kingdom . |
| 9310744 | 6/1993 | WIPO . |

OTHER PUBLICATIONS

English language Derwent Abtract of FR–A–2519251, Jul. 8, 1983.
English language Derwent Abtract of FR–A–2362112, Mar. 17, 1978.

*Primary Examiner*—Caroline D. Liott
*Attorney, Agent, or Firm*—Finnegan, Henderson, Farabow, Garrett & Dunner, L.L.P.

[57] ABSTRACT

An oxidation dyeing composition for keratinous fibres, in particular human keratinous fibres such as hair, of the type comprising a medium suitable for dyeing, the medium containing at least one first para-phenylenediamine oxidation dye precursor containing a primary, secondary or tertiary amine function; at least one first meta-phenylenediamine coupling agent; and either at least one second para-aminophenol oxidation dye precursor or at least one second meta-aminophenol coupling agent; or the acid addition salts thereof. The use of this composition for dyeing keratinous fibres, in particular human keratinous fibres such as hair.

24 Claims, No Drawings

PROCESSES AND KITS FOR DYEING KERATINOUS FIBERS WITH A PARA-PHENYLENEDIAMINE CONTAINING A PRIMARY, SECONDARY OR TERTIARY AMINE FUNCTION, A META-PHENYLENEDIAMINE, AND A PARA-AMINOPHENOL OR A META-AMINOPHENOL

This is a continuation of application Ser. No. 08/712,183, filed Sep. 11, 1996, now U.S. Pat. No. 5,863,300, which is a continuation of application Ser. No. 08/361,661, filed Dec. 22, 1994, now abandoned, all of which are incorporated herein by reference.

The present invention is directed to a composition for the oxidation dyeing of keratinous fibres, in particular human keratinous fibres such as hair, comprising, in combination, at least one para-phenylenediamine containing a primary, secondary or tertiary amine function, at least one meta-phenylenediamine, and in addition, either a para-aminophenol or a meta-aminophenol, which are of the formulae described in the description which follows. The present invention is also directed to the use of such a composition.

It is known to dye keratinous fibres, in particular human keratinous fibres such as hair, with dye compositions containing oxidation dye precursors, in particular ortho- or para-phenylenediamines, ortho- or para-aminophenols, generally referred to as "oxidation bases," and coupling agents, which are also referred to as coloration modifiers, more particularly meta-phenylenediamines, meta-aminophenols and meta-diphenols, which enable the "background" colorations obtained by the products of condensation of the oxidation bases to be modified and to be enriched with glints.

In the field of oxidation dyeing of hair, oxidation dye precursors and coupling agents which are capable of generating, when they are combined, a coloration ranging from blue to blue-violet or to red-violet, and which have a satisfactory resistance to light, to washing, to inclement weather, to perspiration and to the various treatments to which the hair may be subjected, are actively sought. Hitherto, these "background" colorations have usually been obtained with dyes based on para-phenylenediamine. However, the use of para-phenylenediamine is currently contested for toxicological reasons.

It has been discovered that it is possible to obtain new non-toxic and resistant dyes, which generate intense colorations ranging from blue to blue-violet or to red-violet, by combining a para-phenylenediamine containing a primary, secondary or tertiary amine function with a meta-phenylenediamine, which combination additionally contains either a para-aminophenol or a meta-aminophenol of the structures defined below. This discovery forms the basis of the present invention.

The present invention is thus directed to a composition for the oxidation dyeing of keratinous fibres, in particular human keratinous fibres such as hair, comprising a medium suitable for dyeing, the medium containing (a) at least one first para-phenylenediamine oxidation dye precursor of formula (I):

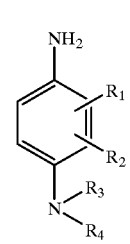

in which:

$R_1$, $R_2$, $R_3$ and $R_4$ have the following meanings:

$R_1$ and $R_2$ represent a hydrogen atom when $R_3$ and $R_4$, which are identical, represent a —$(CH_2)_n$—OH group in which n is equal to 2, 3 or 4; or $R_1$, $R_2$ and $R_3$ represent a hydrogen atom when $R_4$ represents either a —$(CH_2)_n$—$OR_5$ group, in which $R_5$ represents a methyl or ethyl radical, with n being equal to 2 or 3, or a mono- or dihydroxypropyl group; or $R_3$ and $R_4$ represent a hydrogen atom when $R_1$ and $R_2$, which are identical, represent a methyl or ethyl radical and are situated in positions 2,3, 2,5 or 2,6 on the benzene ring; or $R_2$, $R_3$ and $R_4$ represent a hydrogen atom when $R_1$ represents an isopropyl radical, and/or at least one acid addition salt thereof; and (b) at least one first meta-phenylenediamine coupling agent of formula (II):

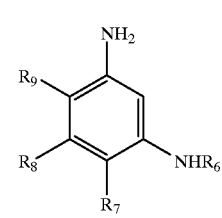

in which:

$R_6$ represents a hydrogen atom, an alkyl radical or a mono- or polyhydroxyalkyl radical; $R_7$ represents a hydrogen atom, an alkyl radical or a monohydroxyalkoxy radical; $R_8$ represents a hydrogen atom or an alkyl radical; $R_9$ represents an alkoxy radical, an aminoalkoxy radical, a mono- or polyhydroxyalkoxy radical or a 2,4-diaminophenoxyalkoxy radical; the above alkyl or alkoxy radicals containing from 1 to 4 carbon atoms; the above mono- or polyhydroxyalkyl radicals and mono- or polyhydroxyalkoxy radicals representing alkyl or alkoxy radicals containing from 2 to 3 carbon atoms and containing from 1 to 3 hydroxyl groups; with the proviso that at least one of the radicals $R_7$ or $R_8$ represents a hydrogen atom; and/or at least one acid addition salt thereof; and either (c) at least one second para-aminophenol oxidation dye precursor of formula (III):

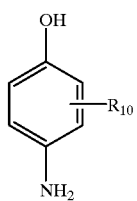

(III)

in which:

$R_{10}$ represents an alkyl, monohydroxyalkyl or monoalkoxyalkyl radical, the alkyl and alkoxy radicals containing from 1 to 4 carbon atoms; and/or at least one acid addition salt thereof; or (d) at least one second meta-aminophenol coupling agent of formula (IV):

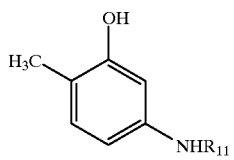

(IV)

in which:

$R_{11}$ represents a hydrogen atom, an alkyl radical containing from 1 to 2 carbon atoms or a hydroxyalkyl radical containing from 2 to 3 carbon atoms; and/or at least one acid addition salt thereof; with the exclusion of:

(i) a composition which simultaneously contains compounds of formulae (I), (II) and (IV) in which $R_1$ and $R_2$ represent a methyl radical in position 2,6 on the benzene ring; $R_3$, $R_4$, $R_6$, $R_7$ and $R_8$ represent a hydrogen atom; $R_9$ represents an aminoethyloxy radical; and $R_{11}$ represents a β-hydroxyethyl group; and (ii) a composition which simultaneously contains compounds of formulae (I), (II) and (IV) in which $R_1$, $R_2$, $R_3$, $R_6$, $R_7$, $R_8$ and $R_{11}$ represent hydrogen; $R_4$ represents a methoxyethyl radical; and $R_9$ represents a β-hydroxyethyloxy group.

The present invention is also directed to a dyeing composition as defined above, for the oxidation dyeing of keratinous fibres, in particular human keratinous fibres, which is a ready-to-use composition, and which also contains an oxidizing agent and has a pH preferably ranging from 3 to 11.

The present invention also contemplates a process for dyeing keratinous fibres, in particular human keratinous fibres, comprising the steps of:

(i) applying to the fibres the dyeing composition as defined above, preferably in at least one composition (A) containing, in a medium suitable for dyeing, the oxidation dye precursors and coupling agents defined above; and (ii) using an oxidizing agent, the oxidizing agent being applied to the-fibres simultaneously with or subsequent to the dyeing composition, to develop the colour of the dyeing composition in an acidic, neutral or alkaline medium. The oxidizing agent can be added only at the moment of use to the composition (A) or can be present in a composition (B) applied simultaneously or sequentially in a separate manner.

The present invention further contemplates a kit or device for dyeing keratinous fibres, in particular human keratinous fibres, comprising at least two compartments, one of the compartments containing a dyeing composition as defined above, and another of the compartments containing a composition (B) containing an oxidizing agent in a medium suitable for dyeing.

A further embodiment of the present invention includes a process for dyeing keratinous fibres, in particular human keratinous fibres, comprising the steps of:

(i) applying to the fibres a dyeing composition as defined above, the dyeing composition being obtained from a kit for dyeing keratinous fibres comprising at least two compartments, one of the compartments containing the dyeing composition as defined above and another of the compartments containing a composition (B) containing an oxidizing agent in a medium suitable for dyeing; and (ii) using the oxidizing agent and the suitable dyeing medium, the agent and the medium being applied to the fibres simultaneously with or subsequent to the dyeing composition, to develop the colour of the dyeing composition in the medium.

The composition and process of the present invention are used for the oxidation dyeing of keratinous fibres in general. The preferred form of keratinous fibres taught by the present invention is human keratinous fibres.

The dyes thus obtained according to the present invention make it possible to achieve intense colorations, ranging from blue to blue-violet or to red-violet, which dyes are non-toxic and are particularly resistant to light, to washing, to inclement weather, to perspiration and to the various treatments to which hair may be subjected. They are, more particularly, very resistant to shampoos. Other characteristics, aspects, aims and advantages of the present invention will emerge more clearly upon reading the description and the examples which follow.

The acid salts which may be used according to the invention are preferably independently chosen from hydrochlorides, sulphates, hydrobromides and tartrates.

According to the invention, as a first oxidation dye precursor, it is preferable to use a para-phenylenediamine of formula (I) which is chosen from the following compounds:

2,6-dimethyl-para-phenylenediamine;
2,6-diethyl-para-phenylenediamine;
2,3-dimethyl-para-phenylenediamine;
2,5-dimethyl-para-phenylenediamine;
2-isopropyl-para-phenylenediamine;
N-(β-methoxyethyl)-para-phenylenediamine;
N,N-di(β-hydroxyethyl)-para-phenylenediamine; and the acid addition salts thereof.

Preferred compounds of formula (II), which defines the metaphenylenediamine coupling agent, include those compounds in which $R_6$ represents a hydrogen atom, an alkyl radical or a hydroxyalkyl radical; $R_7$ and $R_8$ represent a hydrogen atom; $R_9$ represents an alkoxy radical, an aminoalkoxy radical, a hydroxyalkoxy radical or a polyhydroxyalkoxy radical, the alkyl and alkoxy radicals of all these compounds containing from 1 to 4 carbon atoms, with the exception of the polyhydroxyalkoxy group in which the alkoxy radical contains from 2 to 3 carbon atoms and from 1 to 3 hydroxyl radicals. Also preferred are compounds of formula (II) including 1-(β-hydroxyethyloxy)-2,4-diaminobenzene; 1-methoxy-2-amino-4-(β-hydroxyethylamino)benzene; 1-(β-amino-ethyloxy)-2,4-diaminobenzene; 1 1-(β-hydroxyethyloxy)-2-amino-4-(methylamino)benzene; and the acid addition salts thereof. Other preferred compounds of formula (II) include 1-ethyl-2-methoxy-3,5-diaminobenzene; 1-methyl-2-methoxy-3,5-diaminobenzene; 1,3-bis(2,4-diaminophenoxy)propane; 1,3-bis (2,4-diaminophenoxy)methane; 1,2-bis(2,4-diaminophenoxy) ethane; 1,3-diamino-4,6-bis(β-hydroxyethyloxy)benzene; 1-ethoxy-2,4-diamino-5-methylbenzene; 1-methyl-2,4-diamino-5-(β-hydroxyethyloxy)benzene; and the acid addition salts thereof. It is more preferable to use meta-phenylenediamines of formula (II) corresponding to the following compounds: 1- (β-(hydroxyethyloxy) -2,4-diaminobenzene; 1-mnethoxy-2-amino-4-(β-hydroxyethylamino)-benzene, and the acid addition salts thereof.

In the formula (III), which defines the para-aminophenol oxidation dye precursor, the alkyl radical preferably represents a methyl, ethyl, propyl, isopropyl, butyl, sec-butyl or tert-butyl radicals; and the hydroxyalkyl and monoalkoxyalkyl radicals preferably represent —$CH_2OH$; —$CH_2$—$CH_2OH$; —$CH_2$—CHOH—$CH_2OH$; —$CH_2$—CHOH—$CH_3$; or —$CH_2OCH_3$. It is more preferable to use para-aminophenols of formula (III) which correspond to the following compounds:

3 -methyl-4-aminophenol;

3-ethyl-4-aminophenol;

3-hydroxymethyl-4-aminophenol;

2-methyl-4-aminophenol;

2-hydroxymethyl-4-aminophenol;

3-methoxymethyl-4-aminophenol;

2-methoxymethyl-4-aminophenol, and the acid addition salts thereof.

In the formula (IV), which defines the meta-aminophenol coupling agent, the alkyl radical preferably represents methyl or ethyl radicals; and the hydroxyalkyl radical preferably represents —$CH_2$—$CH_2OH$ or —$CH_2$—$CH_2$—$CH_2OH$. It is more preferable to use meta-aminophenols of formula (IV) corresponding to the following compounds:

2-methyl-5-aminophenol;

2-methyl-5-N-methylaminophenol;

2-methyl-5-N-ethylaminophenol;

2-methyl-5-N-(β-hydroxyethylamino)phenol;

2-methyl-5-N-(γ-hydroxypropylamino) phenol, and the acid addition salts thereof.

Oxidation dye compositions of the present invention which are preferred are those which contain, in a medium suitable for dyeing, at least:

one compound (a) being a first oxidation dye precursor;

one compound (b) being a first coupling agent; and one compound (c) being either a second oxidation dye precursor or a second coupling agent, each being of the respective formulae (I), (II), (III) and (IV) as defined above. Compounds (a), (b) and (c) may preferably be chosen from the following compounds:

(a)1: 2,6-dimethyl-para-phenylenediamine;

(a)2: 2,6-diethyl-para-phenylenediamine;

(a)3: 2,3-dimethyl-para-phenylenediamine;

(a)4: 2 -isopropyl-para-phenylenediamine;

(a)5: N,N-di(β-hydroxyethyl)-para-phenylenediamine;

(a)6: N-(β-methoxyethyl)-para-phenylenediamine;

(b)1: 1-(β-hydroxyethyloxy)-2,4-diaminobenzene;

(b)2: 1-methoxy-2-amino-4-(β-hydroxyethylamino) benzene;

(c)1: 2-methyl-5-N-(β-hydroxyethylamino)phenol;

(c) 2: 2-methyl-5-aminophenol;

(c)3: 3-methyl-4-aminophenol; and the acid addition salts thereof.

Compositions for the oxidization dyeing of keratinous fibres, in particular human keratinous fibres, which are preferred according to the present invention correspond to the following combinations:

(a)1+(b)1+(c)1; (a)1+(b)1+(c)2; (a)1+(b)1+(c)3;

(a)2+(b)1+(c)1; (a)2+(b)1+(c)2;

(a)2+(b)1+(c)3; (a)3+(b)1+(c)1; (a)3+(b)1+(c)2;

(a)3+(b)1+(c)3; (a)4+(b)1+(c)1;

(a)4+(b)1+(c)2; (a)4+(b)1+(c)3; (a)5+(b)1+(c)1;

(a)5+(b)1+(c)2; (a)5+(b)1+(c)3;

(a)6+(b)1+(c)1; (a)6+(b)1+(c)3; (a)1+(b)2+(c)1;

(a)1+(b)2+(c)2; (a)1+(b)2+(c)3;

(a)2+(b)2+(c)1; (a)2+(b)2+(c)2; (a)2+(b)2+(c)3;

(a)3+(b)2+(c)1; (a)3+(b)2+(c)2;

(a)3+(b)2+(c)3; (a)4+(b)2+(c)1; (a)4+(b)2+(c)2;

(a)4+(b)2+(c)3; (a)5+(b)2+(c)1;

(a)5+(b)2+(c)2; (a)5+(b)2+(c)3; (a)6+(b)2+(c)1;

(a)6+(b)2+(c)2; and (a)6+(b)2+(c)3.

In the oxidation dye compositions according to the present invention the amount of a first para-phenylenediamine oxidation dye precursor of formula (I), or an acid addition salt thereof, preferably ranges from approximately 0.01 to 10% by weight, and more preferably ranges from 0.05% to 5% by weight, relative to the total weight of the composition; the amount of a first meta- phenylenediamine coupling agent of formula (II), or an acid addition salt thereof, preferably ranges from approximately 0.001% to 3% by weight, and more preferably ranges from 0.005% to 2% by weight, relative to the total weight of the composition; the amount of a second para-aminophenol oxidation dye precursor of formula (III), or an acid addition salt thereof, preferably ranges from approximately 0.01% to 5% by weight, and more preferably ranges from 0.05% to 3% by weight, relative to the total weight of the composition; and the amount of a second meta-aminophenol coupling agent of formula (IV), or an acid addition salt thereof, preferably ranges from approximately 0.005% to 5% by weight, and more preferably ranges from 0.01% to 3% by weight, relative to the total weight of the composition.

The oxidizing agent may preferably be chosen from hydrogen peroxide, urea peroxide, alkali metal bromates and persalts such as perborates and persulphates. It is more preferable to use hydrogen peroxide as the oxidizing agent.

Composition (A), which contains the combination of dyes as described above, may have a pH which preferably ranges from 3 to 11. The pH may be adjusted to the desired value either by using basifying agents which are usually used in dyeing keratinous fibres, such as aqueous ammonia, alkali metal carbonates, alkanolamines, for example mono-, di- and triethanolamines and the derivatives thereof, sodium hydroxide or potassium hydroxide, or the compounds of formula:

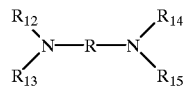

in which R is a propylene residue which is optionally substituted with a hydroxyl group or with a $C_1$–$C_4$ alkyl radical; $R_{12}$, $R_{13}$, $R_{14}$ and $R_{15}$ represent, simultaneously or independently of each other, a hydrogen atom, a $C_1$–$C_4$ alkyl radical or a $C_1$–$C_4$ hydroxyalkyl radical; or by using standard acidifying agents such as inorganic or organic acids, for example hydrochloric acid, tartaric acid, citric acid and phosphoric acid.

The pH of the composition (B) containing the oxidizing agent as defined above is such that, after mixing with the composition (A), the pH of the composition applied to the keratinous fibres, in particular human keratinous fibres, preferably ranges from 3 to 11. The pH can be adjusted to the desired value using acidifying agents, or possibly basifying agents, which are well-known in the state of the art, such as those described above. The oxidizing composition (B) preferably comprises a solution of hydrogen peroxide.

According to a preferred embodiment of the dyeing process or the invention, the dye composition (A) described above is mixed, at the time of use, with an oxidizing solution in a sufficient amount to develop a coloration. The mixture obtained is then applied to keratinous fibres, preferably human keratinous fibres, and is left to stand for preferably 5 to 40 minutes, and more preferably, for 15 to 30 minutes, after which the fibres are rinsed, washed with shampoo, rinsed again and dried.

In addition to the dyes defined above, the dye compositions may also contain other direct dyes and/or coupling agents, especially in order to modify the shades or to enrich the shades with glints.

In another preferred embodiment, the dye compositions may also contain anionic, cationic, nonionic and amphoteric surface-active agents which are well-known in the state of the art, or mixtures thereof, in proportions preferably ranging from approximately 0.5% to 55% by weight, and more preferably from 2% to 50% by weight, relative to the total weight of the composition.

The dye compositions may also contain organic solvents. Preferred organic solvents include $C_1$–$C_4$ lower alkanols such as ethanol and isopropanol; glycerol; glycols or glycol ethers such as 2-butoxyethanol, propylene glycol, diethylene glycol monoethyl ether and monomethyl ether; and aromatic alcohols such as benzyl alcohol or phenoxyethanol; and analogous products and mixtures thereof. These solvents may be present in proportions preferably ranging from approximately 1% to 40% by weight, and more preferably ranging from 5% to 30% by weight, relative to the total weight of the composition.

It is also possible to add thickening agents to the dye composition which are preferably chosen, for example, from sodium alginate, gum arabic, optionally cross-linked acrylic acid polymers, cellulose derivatives, biopolysaccharides such as xanthan gum, or inorganic thickening agents such as bentonite. The thickening agents may be present in proportions preferably ranging from approximately 0.1% to 5% by weight, and more preferably from 0.2% to 3% by weight, relative to the total weight of the composition.

Antioxidants may also be introduced. The antioxidants may preferably be chosen from sodium sulphite, thioglycolic acid, thiolactic acid, sodium bisulphite, dehydroascorbic acid, hydroquinone, 2-methylhydroquinone, tert-butylhydroquinone and homogentisic acid, and may be present in proportions preferably ranging from approximately 0.05% to 1.5% by weight relative to the total weight of the composition.

The dye compositions may also contain other cosmetically acceptable adjuvants, such as, for example, penetration agents, sequestering agents, fragrances, buffers, dispersing agents, treatment agents, conditioning agents, film-forming agents, preserving agents and opacifying agents.

The composition to be applied to the hair may preferably be provided in various forms, such as in the form of a liquid, a cream or a gel or any other form which is suitable for dyeing keratinous fibres, in particular human keratinous fibres such as hair. The dye composition may preferably be packaged under pressure in an aerosol can in the presence of a propellant and may be capable of forming a foam.

Concrete examples illustrating the invention will now be given. To begin with, definitions will be given of the tests used to evaluate the performance of the oxidation dyes according to the invention, with regard to the resistance to perspiration, to light, to shampoos, to inclement weather or to permanent-waving.

Resistance to Perspiration:

A synthetic sweat solution of the following composition was used: 10 g of NaCl, 1 g of potassium hydrogen phosphate, 0.25 g of histidine, lactic acid to give pH=3.2 and distilled water to complete to 100 g.

The locks of dyed hair were immersed in the sweat solution contained in a crystallizing dish which was covered with a watch glass, and they were left for a period of 20 to 50 hours at 37° C. The locks were then rinsed and dried.

Resistance to Light (Xenotest):

The dyed hair was attached to a support (cardboard or plastic). These supports were arranged on sample holders which rotated around a xenon lamp for a period-ranging from 20 to 80 hours, at a moisture content which ranged from 25% to 75% RH (Relative Humidity) and at a temperature of 25° C.

Resistance to Shampoos (Ahiba-Texomat Machine):

Locks of dyed hair were placed in a basket which was immersed in a solution of a standard shampoo. The basket was subjected to an up-and-down movement of variable frequency as well as a rotational movement, which reproduced the action of manual rubbing, which thereby caused the formation of foam.

After being treated for 3 minutes, the locks were removed, rinsed, and then dried. The dyed locks may have been subjected to several consecutive shampoo tests.

Resistance to Inclement Weather (Combined Test):

The dyed locks were exposed to strong light (Xenotest 40 h), at a relative humidity of 60%, and simultaneously, every 12 hours and for a duration of 20 minutes, they were sprayed with water.

Resistance to Permanent-Waving:

The dyed locks were immersed in a Dulcia Vital permanent-wave reducing solution (L'Oréal), of strength ranging from 1 to 3, for a duration of time ranging from 10 to 20 minutes; the locks were rinsed; they were then soaked in a fixing (oxidizing) solution for 5 minutes. After rinsing with water, washing with standard shampoo and rinsing with water again, they were dried.

EXAMPLES 1 TO 10:

10 dye compositions in accordance with the invention were prepared as follows:

| | |
|---|---|
| Dyes (see Tables I and II) | x g |
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oleyl amine containing 2 mol of ethylene oxide, sold under the name Ethomeen 012 by the company AKZO | 7.0 g |
| Diethylaminopropyl laurylaminosuccinamate sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.46 g AM |
| Ammonium acetate | 0.8 g |
| Antioxidant, sequestering agent | qs |
| Fragrance, preserving agent | qs |
| Aqueous ammonia containing 20% of $NH_3$ | 10.0 g |
| Demineralized water qs | 100 g |

At the time of use, each of these compositions was mixed weight for weight with 20 volumes of hydrogen peroxide (6% by weight), which had a pH of 3. A mixture which had a pH of 9.8 was thus obtained. This mixture was then applied to grey hair containing 90% white hairs, which hair was either natural or permanent-waved, for 30 minutes. After rinsing, washing with shampoo, rinsing and drying, the hair was then dyed shades ranging from blue to blue-violet or to red-violet, which shades were determined with MUNSELL numerical values (ASTM Standard D 1535-68) on a MINOLTA CM 2002 calorimeter, and which values are indicated in Table III below.

The inventors believe that these shades should show good resistances, in particular to shampoo.

TABLE I

| EXAMPLES Dyes (g) | 1 | 2 | 3 | 4 | 5 |
|---|---|---|---|---|---|
| N-(β-methoxyethyl)-para-phenylene-diamine. 2HCl | 0.8 | 0.6 | | | |
| 2,3-dimethyl-para-phenylenediamine.2HCl | | | | 0.9 | |
| 2,6-dimethyl-para-phenylenediamine.2HCl | | | | | 0.7 |
| N,N-di (β-hydroxyethyl)-para-phenylene-diamine. $H_2SO_4.H_2O$ | | | 0.6 | | |
| 1-methoxy-2-amino-4-(β-hydroxyethyl-amino) benzene.2HCl | 0.5 | | | 0.6 | 0.5 |
| 1-(β-hydroxyethyloxy)-2,4-diamino-benzene.2HCl | | 0.6 | | | |
| 1,3-bis (2,4-diaminophenoxy) ethane.4HCl | | | 0.3 | | |
| 2-methyl-5-N-(β-hydroxyethylamino)-phenol | 0.3 | | | 0.4 | 0.5 |
| 2-hydroxymethyl-4-aminophenol | | | 0.35 | | |
| 3-methyl-4-aminophenol | | | 0.5 | | |

TABLE II

| EXAMPLES Dyes (g) | 6 | 7 | 8 | 9 | 10 |
|---|---|---|---|---|---|
| 2-isopropyl-para-phenylenediamine.2HCl | 0.6 | | | | |
| 1-methoxy-2-amino-4-N-(β-hydroxyethyl-amino) benzene.2HCl | | | | 0.1 | 0.1 |
| 1-(β-hydroxyethyloxy)-2,4-diamino-benzene.2HCl | 0.05 | 0.4 | 0.5 | | |
| 5-amino-2-methylphenol | 0.45 | 0.4 | | 0.6 | |
| 2-methyl-5-N-(5-β-hydroxyethylamino)-phenol | | | | | 0.5 |
| N-(β-methoxyethyl)-para-phenylene-diamine.2HCl | | | | 0.6 | |
| 2,6-dimethyl-papa-phenylenediamine.2HCl | | 0.7 | 0.5 | | 0.45 |
| 3-methyl 4-aminophenol | | | 0.4 | | |

TABLE III

| | MINOLTA CM 2002 MUNSELL SHADES | |
|---|---|---|
| EXAMPLES | NATURAL HAIR | PERMANENT-WAVED HAIR |
| 1 | 5.6 PB 2.6/2.4 | 7.2 PB 2.0/1.9 |
| 2 | 1.7 P 2.6/0.9 | 0.6 P 2.3/1.0 |
| 3 | 1.0 PB 3.3/1.0 | 4.6 PB 2.3/1.1 |
| 4 | 6.1 PB 2.8/1.5 | 7.0 PB 2.4/1.7 |
| 5 | 7.3 PB 2.4/1.8 | 8 PB 2.0/1.3 |
| 6 | 1.7 RP 3.2/1.6 | 9.7 P 2.4/1.8 |
| 7 | 8.0 PB 2.6/1.6 | 8.4 PB 2.0/1.3 |
| 8 | 2.4 P 2.6/1.2 | 2.1 P 2.0/1.0 |
| 9 | 2.3 P 2.8/1.9 | 9.9 PB 2.2/2.2 |
| 10 | 7.5 P 3.3/0.9 | 3.9 P 2.7/1.3 |

What is claimed is:

1. A process for dyeing keratinous fibres, comprising:
   (i) applying to said fibres a dyeing composition comprising a medium suitable for dyeing, said medium containing
      (a) at least one first para-phenylenediamine oxidation dye precursor selected from a compound of formula (I):

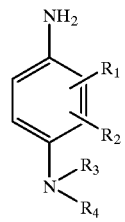

(I)

in which
   $R_1$, $R_2$, $R_3$ and $R_4$ have the following meanings:
      $R_1$ and $R_2$ represent a hydrogen atom when $R_3$ and $R_4$, which are identical, represent a —$(CH_2)_n$—OH group in which n is equal to 2, 3 or 4;
      $R_1$, $R_2$, and $R_3$ represent a hydrogen atom when $R_4$ represents either a —$(CH_2)_n$—$OR_5$ group, in which $R_5$ represents a methyl or ethyl radical, with n being equal to 2 or 3, or a mono- or dihydroxypropyl group; or
      $R_3$ and $R_4$ represent a hydrogen atom when $R_1$ and $R_2$, which are identical, represent a methyl or ethyl radical and are situated in positions 2,3, 2,5, or 2,6 on the benzene ring; and an acid addition salt of said compound of formula (I);
      (b) at least one first meta-phenylenediamine coupling agent

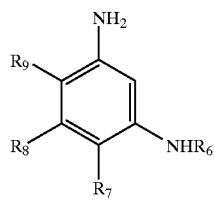

(II)

in which:
R$_6$ represents a hydrogen atom, an alkyl radical or a mono- or polyhydroxyalkyl radical;
R$_7$ represents a hydrogen atom, an alkyl radical or a monohydroxyalkoxy radical;
R$_8$ represents a hydrogen atom or an alkyl radical; and
R$_9$ represents an alkoxy radical, an aminoalkoxy radical, a mono- or polyhydroxyalkoxy radical or a 2,4-diaminophenoxyalkoxy radical;
said alkyl or alkoxy radicals containing from 1 to 4 carbon atoms; said mono- or polyhydroxyalkyl radicals and mono- or polyhydroxyalkoxy radicals independently representing alkyl or alkoxy radicals containing from 2 to 3 carbon atoms and containing from 1 to 3 hydroxyl groups; with the proviso that at least one of the radicals R$_7$ or R$_8$ represents a hydrogen atom;
and an acid addition salt of said compound of formula (II); and
(c) at least one second para-aminophenol oxidation dye precursor selected from a compound of formula (III):

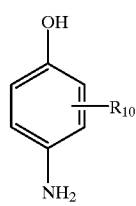

(III)

in which:
R$_{10}$ represents an alkyl, monohydroxyalkyl or monoalkoxyalkyl radical; said alkyl and alkoxy radicals containing from 1 to 4 carbon atoms; and an acid addition salt of said formula (III); and
(ii) developing the color of said dyeing composition in an acidic, neutral or alkaline medium by applying an composition (B) agent to said fibres simultaneously with or subsequent to said dyeing composition.

2. A process according to claim 1, wherein said oxidizing agent is added to said dyeing composition at the time of applying in said step (i).

3. A process according to claim 1, wherein said oxidizing agent is separately contained in a composition (B) and is separately applied to said fibres simultaneously with said dyeing composition.

4. A process according to claim 1, wherein said oxidizing agent is separately contained in a composition (B) and separately applied to said fibers subsequent to said application of said dyeing composition.

5. A process according to claim 1, wherein said keratinous fibres are human keratinous fibres.

6. The process according to claim 1, wherein the dyeing composition contains said first para-phenylenediamine oxidation dye precursor of formula (I) in a weight proportion ranging from 0.01% to 10%, said first meta-phenylenediamine coupling agent of formula (II) in a weight proportion ranging from 0.001% to 3%; and said second para-aminophenol oxidation dye precursor of formula (Ill) in a weight proportion ranging from 0.01% to 5%, said weight proportions being relative to the total weight of the dyeing composition.

7. A process for dyeing keratinous fibres, comprising:
(i) applying to said fibres a dyeing composition comprising a medium suitable for dyeing, said medium containing
(a) at least one first para-phenylenediamine oxidation dye precursor selected from a compound of formula (I):

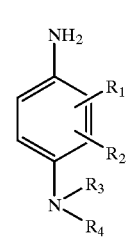

(I)

in which
R$_1$, R$_2$, R$_3$ and R$_4$ have the following meanings:
R$_1$ and R$_2$ represent a hydrogen atom when R$_3$ and R$_4$, which are identical, represent a —(CH$_2$)$_n$—OR group in which n is equal to 2, 3 or 4;
R$_1$, R$_2$, and R$_3$ represent a hydrogen atom when R$_4$ represents either a —(CH$_2$)$_n$—OR$_5$ group, in which R$_5$ represents a methyl or ethyl radical, with n being equal to 2 or 3, or a mono- or dihydroxypropyl group; or
R$_3$ and R$_4$ represent a hydrogen atom when R$_1$ and R$_2$, which are identical, represent a methyl or ethyl radical and are situated in positions 2,3, 2,5, or 2,6; on the benzene ring; or
R$_2$, R$_3$, and R$_4$ represent a hydrogen atom when R$_1$ represents an isopropyl radical;
and an acid addition salt of said compound of formula (I);
(b) at least one first meta-phenylenediamine coupling agent selected from a compound of formula (II):

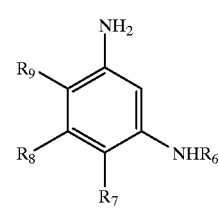

(II)

in which:
R$_6$ represents a hydrogen atom, an alkyl radical or a mono- or polyhydroxyalkyl radical;
R$_7$ represents a hydrogen atom, an alkyl radical or a monohydroxyalkoxy radical;
R$_8$ represents a hydrogen atom or an alkyl radical; and
R$_9$ represents an alkoxy radical, an aminoalkoxy radical, a mono- or polyhydroxyalkoxy radical or a 2,4- diaminophenoxyalkoxy radical; said alkyl or alkoxy radicals containing from 1 to 4 carbon atoms; said mono- or polyhydroxyalkyl radicals and mono- or polydroxyalkoxy radicals independently representing alkyl or alkoxy radicals containing from 2 to 3 carbon atoms and containing from 1 to 3 hydroxy groups; with the proviso that at least one of the radicals $R_7$ or $R_8$ represents a hydrogen atom;

and an acid addition salt of said compound of formula (II); and (c) at least one second meta-aminophenol coupling agent selected from a compound of formula (IV):

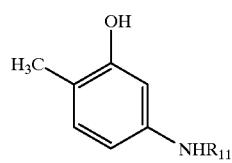

(IV)

in which:

$R_{11}$ represents an alkyl radical containing from 1 to 2 carbon atoms; and an acid addition salt of said compound of formula (IV); and (ii) developing the color of said dyeing composition in an acidic, neutral or alkaline medium by applying an composition (B) agent to said fibres simultaneously with or subsequent to said dyeing composition.

8. The process according to claim 7, wherein said oxidizing agent is added to said dyeing composition at the time of applying in said step (i).

9. The process according to claim 7, wherein said oxidizing agent is separately contained in a composition (B) and is separately applied to said fibres simultaneously with said dyeing composition.

10. The process according to claim 7, wherein said composition (B) agent is separately contained in a composition (B) and is separately applied to said fibres subsequent to said application of said dyeing composition.

11. The process according to claim 7, wherein said keratinous fibres are human keratinous fibres.

12. The process according to claim 7, wherein the dyeing composition contains said first para-phenylenediamine oxidation dye precursor of formula (I) in a weight proportion ranging from 0.01% to 10%, said first meta-phenylenediamine coupling agent of formula (II) in a weight proportion ranging from 0.001% to 3%, and said second meta-aminophenol oxidation dye precursor of formula (IV) in a weight proportion ranging from 0.005% to 5%, said weight proportions being relative to the total weight of the dyeing composition.

13. A kit for dyeing keratinous fibres comprising at least two compartments, one of said compartments containing a dyeing composition comprising a medium suitable for dyeing, said medium containing (a) at least one first para-phenylenediamine oxidation dye precursor selected from a compound of formula (I):

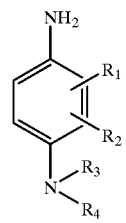

(I)

in which $R_1$, $R_2$, $R_3$ and $R_4$ have the following meanings:

$R_1$ and $R_2$ represent a hydrogen atom when $R_3$ and $R_4$, which are identical, represent a —$(CH_2)_n$—OH group in which n is equal to 2, 3 or 4:

$R_1$, $R_2$, and $R_3$ represent a hydrogen atom when $R_4$ represents either a —$(CH_2)_n$—$OR_5$ group, in which $R_5$ represents a methyl or ethyl radical, with n being equal to 2 or 3, or a mono- or dihydroxypropyl group; or $R_3$ and $R_4$ represent a hydrogen atom when $R_1$ and $R_2$, which are identical, represent a methyl or ethyl radical and are situated in positions 2,3, 2,5, or 2,6 on the benzene ring; and an acid addition salt of said compound of formula (I);

(b) at least one first meta-phenylenediamine coupling agent selected from a compound of formula (II):

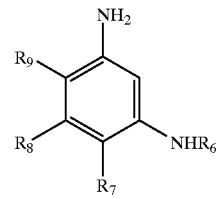

(II)

in which:

$R_6$ represents a hydrogen atom, an alkyl radical or a mono- or polyhydroxyalkyl radical;

$R_7$ represents a hydrogen atom, an alkyl radical or a monohydroxyalkoxy radical;

$R_8$ represents a hydrogen atom or an alkyl radical; and $R_9$ represents an alkoxy radical, an aminoalkoxy radical, a mono- or polyhydroxyalkoxy radical or a 2,4-diaminophenoxyalkoxy radical;

said alkyl or alkoxy radicals containing from 1 to 4 carbon atoms; said mono- or polyhydroxyalkyl radicals and mono- or polyhydroxyalkoxy radicals independently representing alkyl or alkoxy radicals containing from 2 to 3 carbon atoms and containing from 1 to 3 hydroxyl groups; with the proviso that at least one of the radicals $R_7$ or $R_8$ represents a hydrogen atom;

and an acid addition salt of said compound of formula (II); and (c) at least one second para-aminophenol oxidation dye precursor selected from a compound of formula (III):

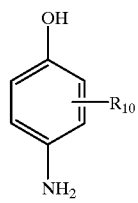

(III)

in which:

R$_{10}$ represents an alkyl, monohydroxyalkyl or monoalkoxyalkyl radical; said alkyl and alkoxy radicals containing from 1 to 4 carbon atoms; and an acid addition salt of said formula (III); and another of said compartments containing a composition (B) containing an oxidation agent in a medium suitable for dyeing.

14. A kit according to claim 13, wherein said keratinous fibres are human keratinous fibres.

15. A kit for dyeing keratinous fibres comprising at least two compartments, one of said compartments containing a dyeing composition comprising a medium suitable for dyeing, said medium containing (a) at least one first para-phenylenediamine oxidation dye precursor selected from a compound of formula I:

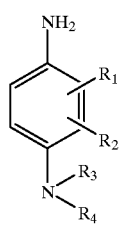

(I)

in which R$_1$, R$_2$, R$_3$ and R$_4$ have the following meanings:

R$_1$ and R$_2$ represent a hydrogen atom when R$_3$ and R$_4$, which are identical, represent a —(CH$_2$)$_n$—OR group in which n is equal to 2, 3 or 4;

R$_1$, R$_2$, and R$_3$ represent a hydrogen atom when R$_4$ represents either a —(CH$_2$)$_n$—OR$_5$ group, in which R$_5$ represents a methyl or ethyl radical, with n being equal to 2 or 3, or a mono- or dihydroxypropyl group; or R$_3$ and R$_4$ represent a hydrogen atom when R$_1$ and R$_2$, which are identical, represent a methyl or ethyl radical and are situated in positions 2,3, 2,5, or 2,6 on the benzene ring; or R$_2$, R$_3$, and R$_4$ represent a hydrogen atom when R$_1$ represents an isopropyl radical;

and an acid addition salt of said compound of formula (I);

(b) at least one first meta-phenylenediamine coupling agent selected from a compound of formula (II):

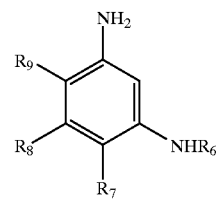

(II)

in which:

R$_6$ represents a hydrogen atom, an alkyl radical or a mono- or polyhydroxyalkyl radical;

R$_7$ represents a hydrogen atom, an alkyl radical or a monohydroxyalkoxy radical;

R$_8$ represents a hydrogen atom or an alkyl radical; and

R$_9$ represents an alkoxy radical, an aminoalkoxy radical, a mono- or polyhydroxyalkoxy radical or a 2,4-diaminophenoxyalkoxy radical; said alkyl or alkoxy radicals containing from 1 to 4 carbon atoms; said mono- or polyhydroxyalkyl radicals and mono- or polydroxyalkoxy radicals independently representing alkyl or alkoxy radicals containing from 2 to 3 carbon atoms and containing from 1 to 3 hydroxy groups; with the proviso that at least one of the radicals R$_7$ or R$_8$ represents a hydrogen atom;

and an acid addition salt of said compound of formula (II); and (c) at least one second meta-aminophenol coupling agent selected from a compound of formula (IV):

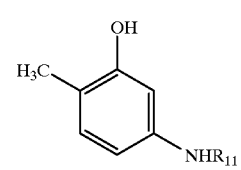

(IV)

in which:

R$_{11}$ represents an alkyl radical containing from 1 to 2 carbon atoms; and an acid addition salt of said compound of formula (IV); and another of said compartments containing a composition (B) containing an oxidation agent in a medium suitable for dyeing.

16. A kit according to claim 15, wherein said keratinous fibres are human keratinous fibres.

17. A process for dyeing keratinous fibres, comprising:

(i) applying to said fibres a dyeing composition comprising a medium suitable for dyeing, said medium containing (a) at least one first para-phenylenediamine oxidation dye precursor selected from a compound of formula (I):

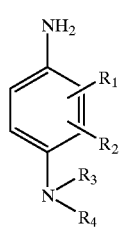

(I)

in which $R_1$, $R_2$, $R_3$ and $R_4$ have the following meanings:

$R_1$ and $R_2$ represent a hydrogen atom when $R_3$ and $R_4$, which are identical, represent a —$(CH_2)_n$—OH group in which n is equal to 2, 3 or 4;

$R_1$, $R_2$, and $R_3$ represent a hydrogen atom when $R_4$ represents either a —$(CH_2)_n$—$OR_5$ group, in which $R_5$ represents a methyl or ethyl radical, with n being equal to 2 or 3, or a mono- or dihydroxypropyl group; or $R_3$ and $R_4$ represent a hydrogen atom when $R_1$ and $R_2$, which are identical, represent a methyl or ethyl radical and are situated in positions 2,3, 2,5, or 2,6 on the benzene ring; and an acid addition salt of said compound of formula (I);

(b) at least one first meta-phenylenediamine coupling agent selected from a compound of formula (II):

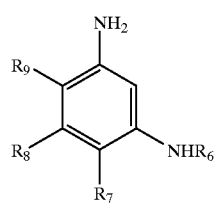

(II)

in which:

$R_6$ represents a hydrogen atom, an alkyl radical or a mono- or polyhydroxyalkyl radical;

$R_7$ represents a hydrogen atom, an alkyl radical or a monohydroxyalkoxy radical;

$R_8$ represents a hydrogen atom or an alkyl radical; and $R_9$ represents an alkoxy radical, an aminoalkoxy radical, a mono- or polyhydroxyalkoxy radical or a 2,4-diaminophenoxyalkoxy radical;

said alkyl or alkoxy radicals containing from 1 to 4 carbon atoms; said mono- or polyhydroxyalkyl radicals and mono- or polyhydroxyalkoxy radicals independently representing alkyl or alkoxy radicals containing from 2 to 3 carbon atoms and containing from 1 to 3 hydroxyl groups; with the proviso that at least one of the radicals $R_7$ or $R_8$ represents a hydrogen atom;

and an acid addition salt of said compound of formula (II); and (c) at least one second para-aminophenol oxidation dye precursor selected from a compound of formula (III):

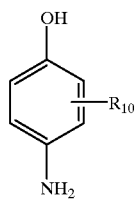

(III)

in which:

$R_{10}$ represents an alkyl, monohydroxyalkyl or monoalkoxyalkyl radical; said alkyl and alkoxy radicals containing from 1 to 4 carbon atoms; and an acid addition salt of said formula (III);

said dyeing composition being obtained from a kit for dyeing keratinous fibres comprising at least two compartments, one of said compartments containing said dyeing composition and another of said compartments containing a composition (B) containing an composition (B) agent in a medium suitable for dyeing; and (ii) developing the color of said dyeing composition in an acidic, neutral or alkaline medium by applying said composition (B) agent to said fibres simultaneously with or subsequent to said dyeing composition.

18. A process according to claim 17, wherein said composition (B) is applied to said fibres simultaneously with said dyeing composition.

19. A process according to claim 17, wherein said composition (B) is applied to said fibres subsequent to said dyeing composition.

20. A process according to claim 17, wherein said keratinous fibres are human keratinous fibres.

21. A process for dyeing keratinous fibres, comprising:

(i) applying to said fibres a dyeing composition comprising a medium suitable for dyeing, said medium containing (a) at least one first para-phenylenediamine oxidation dye precursor selected from a compound of formula (I):

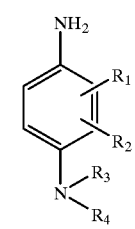

(I)

in which $R_1$, $R_2$, $R_3$ and $R_4$ have the following meanings:

$R_1$ and $R_2$ represent a hydrogen atom when $R_3$ and $R_4$, which are identical, represent a —$(CH_2)_n$—OR group in which n is equal to 2, 3 or 4;

$R_1$, $R_2$, and $R_3$ represent a hydrogen atom when $R_4$ represents either a —$(CH_2)_n$—$OR_5$ group, in which $R_5$ represents a methyl or ethyl radical, with n being equal to 2 or 3, or a mono- or dihydroxypropyl group; or $R_3$ and $R_4$ represent a hydrogen atom when $R_1$ and $R_2$, which are identical, represent a methyl or ethyl radical and are situated in positions 2,3, 2,5, or 2,6 on the benzene ring; or $R_2$, $R_3$, and $R_4$ represent a hydrogen atom when $R_1$ represents an isopropyl radical;

and an acid addition salt of said compound of formula (I);

(b) at least one first meta-phenylenediamine coupling agent selected from a compound of formula (II):

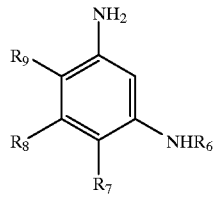

(II)

in which:

$R_6$ represents a hydrogen atom, an alkyl radical or a mono- or polyhydroxyalkyl radical;

$R_7$ represents a hydrogen atom, an alkyl radical or a monohydroxyalkoxy radical;

$R_8$ represents a hydrogen atom or an alkyl radical; and $R_9$ represents an alkoxy radical, an aminoalkoxy radical, a mono- or polyhydroxyalkoxy radical or a 2,4-diaminophenoxyalkoxy radical; said alkyl or alkoxy radicals containing from 1 to 4 carbon atoms; said mono- or polyhydroxyalkyl radicals and mono- or polydroxyalkoxy radicals independently representing alkyl or alkoxy radicals containing from 2 to 3 carbon atoms and containing from 1 to 3 hydroxy groups; with the proviso that at least one of the radicals $R_7$ or $R_8$ represents a hydrogen atom;

and an acid addition salt of said compound of formula (II); and (c) at least one second meta-aminophenol coupling agent selected from a compound of formula (IV):

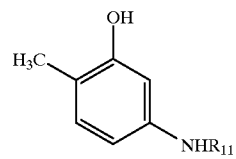

(IV)

in which:

$R_{11}$ represents an alkyl radical containing from 1 to 2 carbon atoms; and an acid addition salt of said compound of formula (IV); said dyeing composition being obtained from a kit for dyeing keratinous fibres comprising at least two compartments, one of said compartments containing said dyeing composition and another of said compartments containing a composition (B) containing an composition (B) agent in a medium suitable for dyeing; and (ii) developing the color of said dyeing composition in an acidic, neutral or alkaline medium by applying said composition (B) to said fibres simultaneously with or subsequent to said dyeing composition.

22. The process according to claim 21, wherein said composition (B) is applied to said fibres simultaneously with said dyeing composition.

23. The process according to claim 21, wherein said composition (B) is applied to said fibres subsequent to said dyeing composition.

24. The process according to claim 21, wherein said keratinous fibres are human keratinous fibres.

* * * * *